United States Patent [19]
Stokes et al.

[11] Patent Number: 5,318,795
[45] Date of Patent: Jun. 7, 1994

[54] STAINING METHODS FOR HISTOLOGY AND CYTOLOGY SPECIMENS

[75] Inventors: Barry O. Stokes, Logan, Utah; John F. Gibson, La Mirada, Calif.

[73] Assignee: Wescor, Inc., Logan, Utah

[21] Appl. No.: 42,455

[22] Filed: Apr. 5, 1993

Related U.S. Application Data

[63] Continuation of Ser. No. 697,311, May 7, 1991, abandoned.

[51] Int. Cl.$^5$ ............................................... A01N 1/00
[52] U.S. Cl. ............................................... 427/4; 424/3
[58] Field of Search ........................... 427/2, 4; 424/3

[56] References Cited

U.S. PATENT DOCUMENTS

| | | | |
|---|---|---|---|
| 2,581,523 | 1/1952 | Ferrari | 8/3 |
| 3,352,280 | 11/1967 | Hughes et al. | 118/9 |
| 3,389,052 | 6/1968 | Ehrenreich et al. | 167/84.5 |
| 3,440,317 | 4/1969 | Martinez | 424/3 |
| 4,089,989 | 5/1978 | White et al. | 427/2 |
| 4,103,041 | 7/1978 | Macho et al. | 427/2 |
| 4,137,299 | 1/1979 | DiMaggio | 424/3 |
| 4,193,980 | 3/1980 | Clason et al. | 427/4 |
| 4,656,047 | 4/1987 | Kok et al. | 427/4 |
| 4,714,606 | 12/1987 | Kass | 424/3 |
| 4,911,915 | 3/1990 | Fredenburgh | 424/3 |
| 5,009,185 | 4/1991 | Stokes et al. | 118/52 |

OTHER PUBLICATIONS

J. S. Drijver, *Acta Cytologica*, vol. 27, No. 2, pp. 210–211 Mar. (1983).

*Primary Examiner*—Shrive Beck
*Assistant Examiner*—Diana L. Dudash
*Attorney, Agent, or Firm*—Mallinckrodt & Mallinckrodt

[57] ABSTRACT

In the field of staining methods for histology and cytology specimens, the improvements of the invention are three-fold. First included is a drying-clearing step whereby a specimen is cleared by drying. Thus, the use of hazardous chemical-clearing agents to remove washing-dehydrating solution prior to cover-slipping is eliminated. Second, in a staining method using spray staining equipment, the use of a low molarity, combination, bluing-washing solution which serves the dual purpose of a washing solution and a bluing reagent, eliminates the use of water in a staining procedure. Third, and also in a staining method using spray staining equipment, the use of a series of sprays of fresh, essentially anhydrous, washing-dehydrating solution to dehydrate a specimen replaces immersion in a series of washing-dehydrating solutions and thereby decreases the amount of chemical consumed and also avoids contamination of the reagent with water and specimen debris.

19 Claims, 2 Drawing Sheets

STAINING METHODS FOR HISTOLOGY AND CYTOLOGY SPECIMENS

This is a continuation of copending application Ser. No. 07/697,311 filed on May 7, 1991, now abandoned.

BACKGROUND OF THE INVENTION

1. Field

The invention is in the field of staining cytology and histology specimens.

2. State of the Art

The field of pathology involves the microscopic examination of fixed cytology specimens (individual cells in a smear or cell block) and histology specimens (cell aggregates that form a structure with a specific function). These specimens are examined to determine if tissue is normal or diseased. A specimen is processed and applied to a microscope slide and then stained to make the normally transparent cells brilliantly colored for easier observation and to distinguish the various cellular elements which have differing affinities for the various stains.

Cytology specimens are prepared by smearing a sample onto a microscope slide and wet fixing with an alcohol solution which usually contains polyethylene glycol [PEG]. Cytocentrifugation may also be used to deposit cells onto slides from dilute cell suspensions, e.g., body fluids. The PEG is removed prior to staining by exposing the specimen to a washing-dehydrating reagent. The washing-dehydrating reagents employed in staining may include alcohols of one to three carbon atoms. Typically ethanol is employed. However, it is possible to use compounds such as glycols, ketones, esters and ethers of from two to about five carbon atoms, or mixtures thereof.

Specimen preparation for histology and cytology samples require different procedures. For histology specimens, the tissue pieces are fixed in a suitable fixative, typically formalin, and embedded in melted paraffin wax. The wax block is then cut on a microtome to yield a thin slice of paraffin containing the tissue. The specimen slice is then applied to a microscope slide, air dried, and heated to cause the specimen to adhere to the glass slide. Residual paraffin is then dissolved with a suitable solvent, typically xylene, toluene, or others. These so-called deparaffinizing solvents are then removed with a washing-dehydrating type reagent prior to staining. Alternatively, slices may be prepared from frozen specimens, fixed briefly in 10% formalin, then infused with dehydrating reagent. Consequently, a common step for both cytology and histology specimens is the removal of the dehydrating reagent prior to staining with an aqueous stain.

The usual method for staining cytology samples is the Papanicolaou staining technique, usually a progressive stain, while the most common method for histologic staining is the hematoxylineosin [H&E] staining technique which is typically a regressive stain. After the initial preparation of the specimen, these methods share common steps and are quite similar in their characteristics.

The typical technique for performing Papanicolaou and H&E staining is the immersion (dip) technique of staining either manually or with the aid of automated equipment. Immersion Papanicolaou staining consists of the following steps with the steps that are omitted from the H&E method indicated:

(a) Removing dehydrating reagent from a specimen affixed to a microscope slide and hydrating the specimen by soaking in water;

(b) Applying hematoxylin for staining the cell nuclei in the specimen;

(c) Removing excess hematoxylin by rinsing with water [For a regressive hematoxylin stain, the water rinse is usually followed by rinsing with an acid-alcohol followed by rinsing with water to remove the acid-alcohol];

(d) Contacting the slide with a concentrated solution having a pH above 5.0 to turn the hematoxylin blue [bluing solution];

(e) Removing the bluing solution by rinsing with water;

(f) [Omitted from H&E method] Staining cytoplasmic elements in the specimen with an alcoholic solution of the dye, orange G, that stains keratinized tissue yellow to orange;

(g) [Omitted from H&E method] Washing away excess orange G by rinsing with a dehydrating reagent;

(h) Staining other cytoplasmic elements with an alcoholic solution of eosin Y, a red stain, and light green or fast green, [Together, this stain combination is the Papanicolaou EA stain. The Papanicolaou EA stain differentiates between superficial cells which stain red and intermediate cells which stain blue to green. The green stain is omitted from the H&E method.];

(i) Removing excess stain and water by a series of sequential washes in a dehydrating reagent;

(j) Contacting the slide with a chemical-clearing agent (toluene, xylene, or t-butanol) to remove residual dehydrating reagent remaining from the washing step;

(k) Applying a cover-slip mountant and a cover-slip after first removing the slide from the chemical-clearing agent. The clearing agent evaporates and the mountant hardens leaving a stained and mounted slide.

As seen from the above steps, the staining of cytology and histology specimens are very similar. However, for clarity's sake the following differences between the handling of histology specimens as compared to cytology specimens are noted:

1. In an H&E method for histology specimens, the hematoxylin in step (d) is usually more concentrated for tissue sections than for cytology specimens. Regressive hematoxylin stain usually employs a more concentrated hematoxylin.
2. In the H&E method, steps (f) and (g) are omitted.
3. The green component of the cytoplasmic stain in step (h) for cytology specimens is omitted when performing an H&E stain on histology specimens.

There are several disadvantages to the prior art immersion staining techniques. The chemical-clearing agents typically employed in the chemical-clearing step include many toxic substances which can harm the environment and present a hazard to laboratory personnel. Furthermore, the immersion staining techniques usually take from fifteen to twenty minutes and include many washes, each performed several times. Still further, the open baths of volatile dehydrating reagents used lead to reagent loss due to vaporization of reagent. Dipping slides into a bath also lends itself to loss of reagents. Dipping in a bath also leads to contamination of the bath with the reagent of the previous step resulting in inefficient use of washing-dehydrating reagents. In addition, cells can come off the slide into the reagent bath and contaminate other specimens, i.e., cross-contamination of specimens.

In the past, the baths of washing-dehydrating reagent typically consisted of three increasingly concentrated ethanol solutions, typically 50%, 75%, and 95%. It was thought that initial exposure to a more dilute solution was needed to reduce shock to the specimen. Current practice is to start with primary, secondary, and tertiary baths of 95% ethanol so that the sequential baths becomes more and more diluted as the number of slides exposed to the bath increases. When the tertiary bath begins to show significant contamination with dye or otherwise becomes diluted it is used as the secondary bath, the secondary bath is then used as the primary bath, and a new, fresh, concentrated tertiary ethanol bath is employed. Current practice has a similar disadvantage to that of the prior practice in that it consists of exposing the slide to essentially a series of three reagent solutions, each increasingly more concentrated than its predecessor.

Improved staining methods for histology and cytology specimens, decreasing the number of steps and the number and quantity of reagents consumed has long been needed, but providing for same has remained a problem. Immersion staining has been automated. However, it has been done by merely adapting the hand staining procedure to be performed by machine without any change in the steps of the procedure. In the related field of staining bacterial specimens, the Gram stain method has been adapted to be performed on automated spray staining equipment, such as the Aerospray® stainer manufactured by Wescor, Inc. of Logan, Utah. However, although the automated spray method of performing the Gram stain solves the contamination problem, it does not teach or suggest how to decrease the number of steps and the number an quantity of reagents consumed in cytology and histology staining procedures.

SUMMARY OF THE INVENTION

The invention comprises an improved method for staining histology and cytology specimens, the improvements and their advantages include:

a) a drying-clearing step whereby a specimen is cleared of dehydrating reagent by drying, thus the use of hazardous chemical-clearing agents to remove dehydrating reagent prior to cover-slipping is eliminated;

b) in a staining procedure using spray staining equipment, the use of a low molarity, combination bluing-washing solution serves the dual purpose of a washing solution and a bluing reagent and eliminates the use of water in a staining procedure; and c) in a staining procedure using spray staining equipment, the use of a series of sprays of fresh, essentially anhydrous dehydrating solution to dehydrate a specimen replaces immersion in a series of baths of dehydrating reagent of differing concentrations and significantly reduces reagent consumption and also avoids contamination of the reagent with water, specimen debris, and potential cross-contamination of specimens.

Together, the improvements decrease the number of steps, the number of reagents, and reagent consumption. In a staining procedure employing these improvements and using automated spray staining equipment, the procedure can be shortened from the usual fifteen to twenty minutes to between about four to twelve minutes.

BRIEF DESCRIPTION OF THE DRAWINGS

The best mode presently contemplated for carrying out the invention commercially is illustrated in the accompanying drawings, in which.

DETAILED DESCRIPTION OF THE PREFERRED EMBODIMENTS

There is enormous routine use of the Pap and H&E stains and the best mode contemplated for the invention is for use with these stains. Additionally, the best mode contemplated for performing the improved staining is by use of automated spray staining equipment. Accordingly, the examples given are of automated spray staining methods for pap and H&E staining for, respectively, cytology and histology specimens.

Once microscope slides have an affixed specimen and are ready to be loaded into an automated spray stainer, such stainer operates according to principles equally applicable to both histology and cytology specimens. An automated spray staining apparatus contemplated for use with the invention includes a centrifuge carousel for holding the slides and rotating them past a spray nozzle which applies reagents. Such equipment is adapted to administer alternating cycles of 1) spraying a reagent on the specimen, and 2) waiting for the applied reagent to diffuse through and interact with the specimen so that the specimen receives a "total exposure" to the reagent sufficient to accomplish the object in applying that particular reagent.

"Total exposure" is here defined as the number of cycles and the total length of time of each cycle of spraying and waiting and is, of course, dependent upon the rotational speed at which the sprays are applied. These parameters comprising the "total exposure" can vary to some extent so long as the exposure is sufficient to accomplish the objective of a given step, the objectives being, e.g., applying a stain to the specimen, washing the excess stain from the specimen, or hydrating or dehydrating the specimen. Likewise, the rotational speed at which the slides are moved past the spray nozzle and the rotational speed applied to remove excess reagent from the slide can vary. For the examples, a spray application of 2 seconds with the centrifuge carousel of the sprayer rotating at about 30 RPM resulted in the slide being sprayed during a single pass before the spray nozzle. A spray period of four seconds resulted in the slide being sprayed during two passes before the spray nozzle, etc. Thus, it should be understood that the spray times, the wait times, and the rotational speeds given below are only an example of a selection of parameters comprising a "total exposure" sufficient to accomplish the individual steps of the staining process. These may be varied and still yield successful staining.

Furthermore, the parameters may be varied to suit individual preferences from a standpoint of timeliness and comparability to generally preferred stain quality. Still further, the parameters can be adjusted to accommodate the precise recipe employed for making up the stains. For the examples, Aerospray® staining reagents obtained from Wescor, Inc., Logan, Utah were employed in Wescor's automated spray staining equipment, the Aerospray® stainer. An embodiment of the Aerospray® stainer is described in U.S. Pat. No. 5,009,185.

Figure 1:
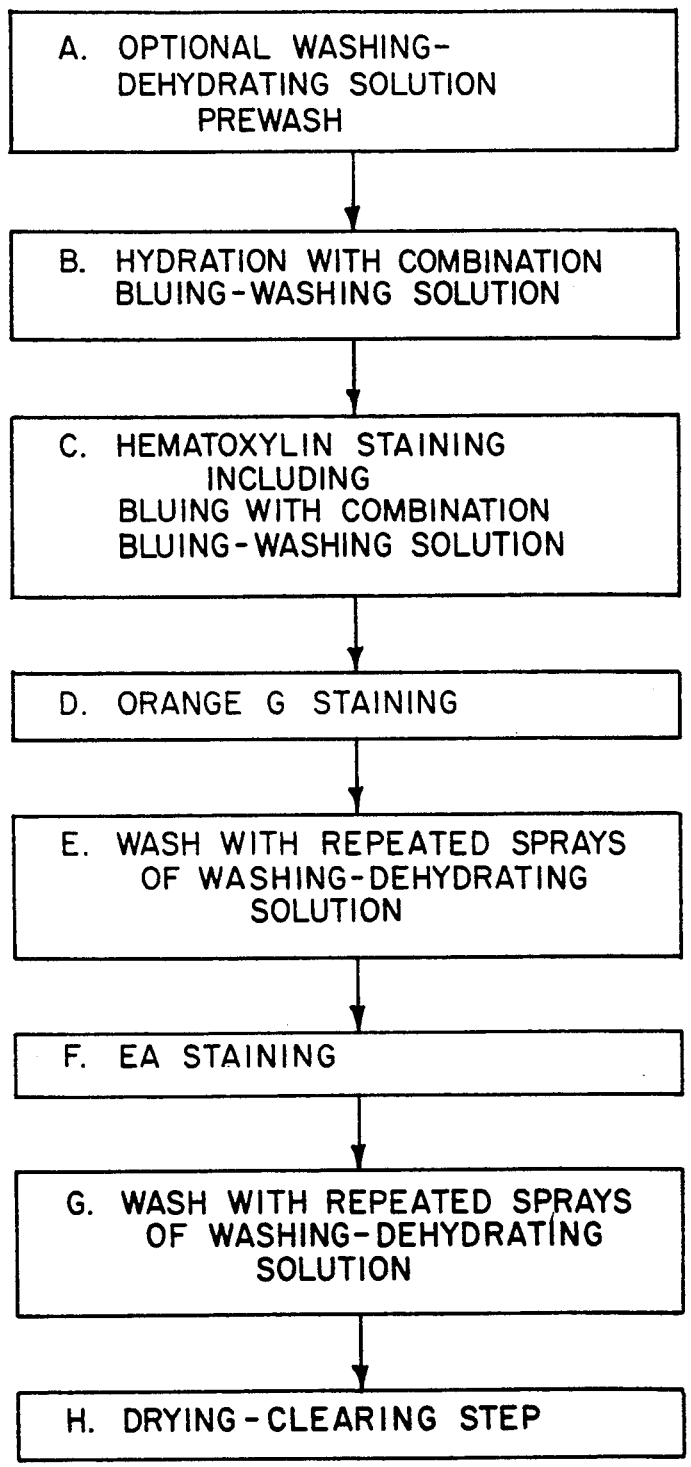
FIG. 1 represents a schematic diagram of the steps employed in performing a method for automated spray staining of cytology specimens (pap staining)

Having thus explained the principles common to both histology and cytology staining, the matter of a specific example of automated pap spray staining may now be considered. In the automated pap spray staining procedure for cytologic specimens given below, the description of the general nature of the step comes after the letter followed by numerals denoting the sequence in which the reagent of the general step is sprayed and the wait time after spraying. FIG. 1 shows the automated steps of a pap spray staining procedure and Example I demonstrates a "total exposure" sufficient to accomplish each step.

EXAMPLE I (a) An optional step of prewashing with anhydrous dehydrating solution for removal of PEG or other residues with the centrifuge speed set at 30 RPM;

| (1) | Spray | about 4 seconds |
|---|---|---|
|     | Wait  | about 2 seconds |
| (2) | Spray | about 2 seconds |
|     | Wait  | about 2 seconds |
| (3) | Spray | about 2 seconds |
|     | Wait  | about 2 seconds |
| (4) | Spray | about 2 seconds |
|     | Wait  | about 2 seconds |
| (5) | Spray | about 2 seconds |
|     | Wait  | about 2 seconds |
| (6) | Spray | about 2 seconds |
|     | Wait  | about 2 seconds |
| (7) | Spray | about 2 seconds |
|     | Wait  | about 2 seconds; |
| (8) | Spray | about 2 seconds |
|     | Wait  | about 2 seconds; |

(b) Washing with bluing-washing solution to remove dehydrating solution and to hydrate the specimen;

| (1) | Spray | about 4 seconds |
|---|---|---|
|     | Wait  | about 4 seconds |
| (2) | Spray | about 4 seconds |
|     | Wait  | about 4 seconds |
| (3) | Spray | about 4 seconds |
|     | Wait  | about 4 seconds |
| (4) | Spray | about 4 seconds |
|     | Wait  | about 4 seconds |
| (5) | Spray | about 4 seconds |
|     | Wait  | about 4 seconds; |

(c) Staining with Hematoxylin stain;

| (1) | Spray | about 4 seconds |
|---|---|---|
|     | Wait  | about 20 seconds |
| (2) | Spray | about 2 seconds |
|     | Wait  | about 20 seconds |
| (3) | Spray | about 2 seconds |
|     | Wait  | about 12 seconds |
| (4) | Spin  | about 1 second at about 1000 RPM to remove excess reagent from slide |
| (5) | Stabilize | about 12 seconds until rotation slows so that the rotation speed can be reset to a spray application speed of about 30 RPM; |

(d) Washing with bluing-washing solution to wash off the hematoxylin and raise the pH to above about 5.0;

| (1) | Spray | about 6 seconds |
|---|---|---|
|     | Wait  | about 10 seconds |
| (2) | Spray | about 4 seconds |
|     | Wait  | about 10 seconds; |

(e) Staining keratinized cells yellow to orange with Orange G stain;

| (1) | Spray | about 4 seconds |
|---|---|---|
|     | Wait  | about 10 seconds |
| (1) | Spray | about 2 seconds |
|     | Wait  | about 10 seconds |
| (3) | Spray | about 2 seconds |
|     | Spin  | about 1 second at 1000 RPM |
| (4) | Stabilize | about 12 seconds, then reset to about 30 RPM; |

(f) Washing with anhydrous dehydrating solution to remove excess orange G;

| (1) | Spray | about 10 seconds |
|---|---|---|

(g) Staining cytoplasm blue and red with Papanicolaou EA stain;

| (1) | Spray | about 4 seconds |
|---|---|---|
|     | Wait  | about 20 seconds |
| (2) | Spray | about 2 seconds |
|     | Wait  | about 20 seconds |
| (3) | Spray | about 2 seconds |
|     | Wait  | about 18 seconds |
| (4) | Spin  | about 1 second at about 1000 RPM to clear excess reagent from slide |
| (5) | Stabilize | about 12 seconds, then reset to about 30 RPM; |

(h) Washing with dehydrating solution to remove excess EA stain;

| (1) | Spray | about 10 seconds |
|---|---|---|
|     | Wait  | about 6 seconds |

(i) Clearing the slide by removing excess dehydrating solution and at least partially drying the slide of dehydrating solution and thereby readying it for the application of a cover-slip mountant and a cover-slip.

| (1) | Spin | about 6 seconds at about 1000 RPM |
|---|---|---|

As demonstrated by Example I, steps (a) through (m) of the prior art dip staining procedure are similar except for three improvements.

One improvement is the new step, herein called the drying-clearing step. Instead of dissolving away any remaining dehydrating solution by the application of a so-called chemical-clearing agent (e.g. xylene, toluene, t-butanol, or others), excess dehydrating solution is removed by drying. It should be understood that the new drying-clearing step may be employed with histology and cytology specimens and in hand and automated dip staining as well as spray staining methods. Also, it should be understood that spray staining methods encompass spray staining by hand using spray equipment, staining in any automated spray staining equipment and especially automated equipment including a centrifuge carousel for holding the slides and rotating them past a spray nozzle which applies reagents.

In the automated spray staining procedure, a few seconds of centrifugal force is applied to produce a slide that is at least partially dry, i.e., slightly damp, with dehydrating solution. Alternatively, it has also been found acceptable to completely dry the slide of dehydrating solution by prolonging the centrifugation up to about 60 seconds at 30 RPM. Still further alternatively, the slide can be cleared by allowing the slide to stand and the dehydrating solution to evaporate or by applying forced air or mild heat to speed evaporation.

Prior art taught that xylene or toluene-based, coverslipping mountant is not miscible with such typical washing-dehydrating agents as either ethanol or isopropanol. Consequently, it was taught that the washing-dehydrating agents had to be removed chemically before application of the cover-slipping mountant or a cloudy artifact would result. The so-called chemical-clearing agents were employed to remove the washing-dehydrating agents. It has been observed that, if the slides are dry or even only slightly damp with dehydrating reagent, suitable mounting without cloudiness occurs. Thus, the step of applying a chemical agent to clear the dehydrating solution previously considered essential has been replaced by removing dehydrating solution by centrifugation or simply allowing the dehydrating solution to evaporate.

Drying of the slides prior to mounting is usually not recommended because it was thought that artifacts in sample morphology would result. J. S. Drijver, *Acta Cytologica*, Volume 27, No. 2, p.210–211 (1983), reported that air drying of pap-stained slides following clearing with t-butanol does not produce deleterious effects to the specimen. Heretofore, so far as is known, no one has reported that air drying after the washing with a dehydrating reagent before chemical-clearing, instead of drying after chemical-clearing, results in adequate clearing of slides and slides that are free of artifacts. Here, the rapid drying of water-miscible dehydrating solution washes achieved by about 20 to 60 seconds of centrifugal force at about 1000 RPM resulted in acceptable mounting without any associated artifacts. Even very short centrifugal clearing time, i.e., about 4–6 seconds of centrifugal force at about 1000 RPM, was found to be adequate even though the specimen contained small amounts of dehydrating solution. At higher rotational speeds, a ventilated centrifuge creates air movement. Thus, it aids the drying of slides by applying forced air. Slower drying by allowing slides wet with dehydrating solution to stand and evaporate also produced no artifacts. Thus, it was found that centrifugal clearing or simple drying of dehydrating solution, i.e., a drying-clearing step, could be substituted for the typical chemical-clearing step of the prior art.

A second improvement is the elimination of the use of water. The washing solution at step (c) of the prior art dip staining procedure is typically water. The step readies the slide for the application of any subsequent reagent. Rather than modifying the automatic spray staining equipment to use water as an additional washing solution, the bluing solution of prior art step (f) is modified to serve as a combination bluing-washing solution. The bluing solution of the prior art is typically a concentrated solution having a pH above 5.0 and is used to turn the hematoxylin blue. The modification also allows the elimination of prior art step (g) which calls for removing the above pH 5.0 solution by rinsing with water The invention employs any solution of above pH 5.0, adequate for bluing, but dilute, i.e., of low molarity, preferably no more than about 0.01 molarity of a suitable solute. Sodium bicarbonate ($NaHCO_3$) is one example of a suitable solute yielding an above pH 5.0 solution that might be employed. Sodium or potassium hydroxides as well as other weak or strong bases may also be employed. The low, less than about 0.01, molarity of the combination bluing-washing agent allows the acidity of the hematoxylin to overpower it when applied in the typical quantities of automatic spray staining equipment. Consequently, the hematoxylin is washed from the slide in the acidic form and does not precipitate on the slide as it normally would if a typical high molarity bluing solution were employed. After the excess hematoxylin is removed, sufficient bluing of the remaining hematoxylin is achieved with exposure to bluing-washing solution administered by the automated spraying equipment, which is typically about five sprays delivered by the Aerospray ® stainer.

Limited evidence suggests a greater molarity of alkaline solution causes undesirable precipitation of hematoxylin on the slide, especially when using the highly concentrated hematoxylin solutions employed in staining tissue sections. Thus, bluing solutions of higher molarity of the prior art were not employed. Also, the low molarity of the solution of the invention eliminates the need to wash off the bluing agent and staining can proceed to the next step without washing.

The advantage of a combination bluing-washing solution is unavailable to the dip staining methods that employ washing by immersion in a solution bath. Dipping into dilute bluing without rinsing the excess hematoxylin from the slide would readily lower the pH and render the bluing solution ineffective. Thus, the dilute, combination, bluing ™ washing solution is only advantageous in the spray staining methods which employs a fresh reservoir of reagent that remains uncontaminated.

Third, there is the improved technique of applying a washing-dehydrating solution to a slide by spraying on a single concentrated solution rather than by immersing the slide in what is essentially a series of baths of differing concentrations of washing-dehydrating solution. At step (k) of the prior art dip staining procedure, the excess Papanicolaou EA stain and water are removed by dipping in a series of baths of washing-dehydrating reagent. The baths become more and more dilute and the primary and secondary baths becoming more dilute more quickly than the tertiary bath so that soon after setting up the three baths of equal concentration, what is actually being employed is a series of increasingly concentrated baths. In the usual next to the final step, the slide is contacted with a chemical-clearing agent to remove the washing-dehydrating chemicals from the previous step. In the improved automated spray staining procedure, the step of dipping in a series of baths of differing concentrations of washing-dehydrating reagent after staining with the Papanicolaou E is replaced. Instead, the slide is repeatedly sprayed with small volumes of fresh, essentially anhydrous, or, at least, concentrated, dehydrating solution. The use of primary, secondary, and tertiary solutions is eliminated.

Figure 2:
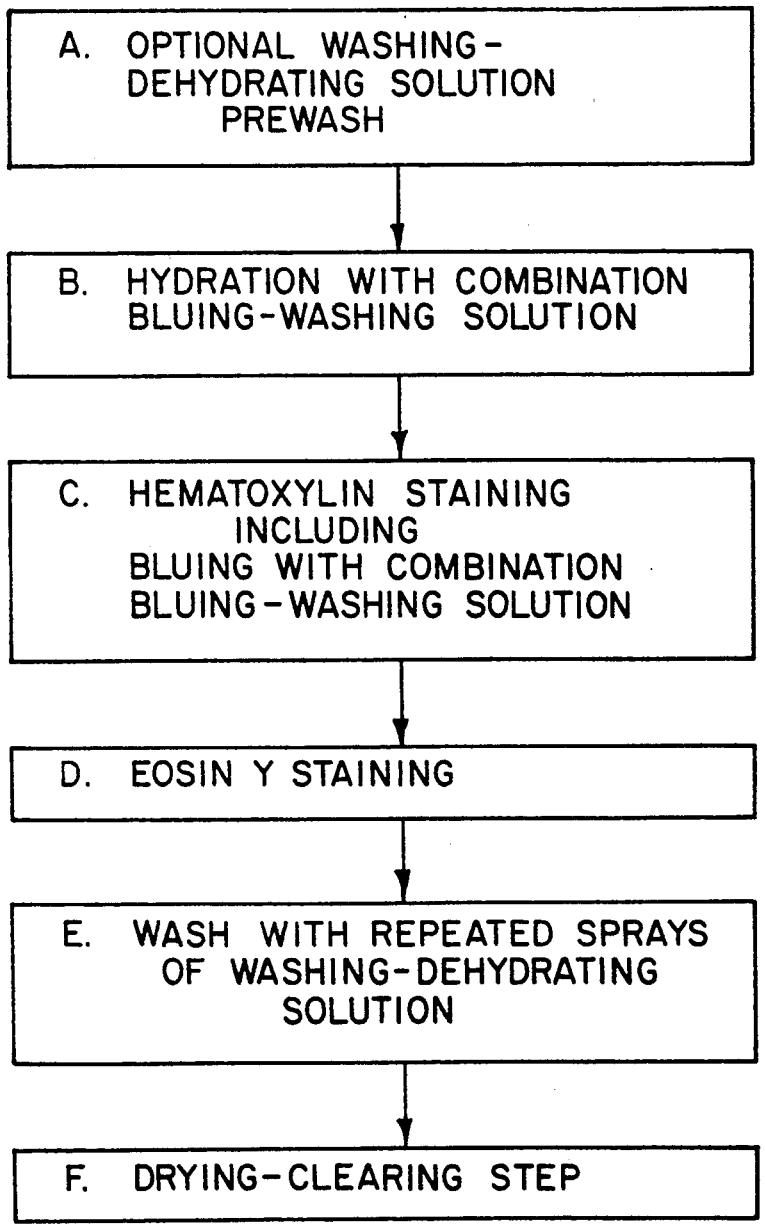
FIG. 2 represents a schematic diagram of the steps employed in performing a method for automated spray staining of histology specimens (H&E staining).

These three improvements can also be employed in an automated spray procedure for applying the H&E stain. FIG. 2 shows the steps of an automated spray procedure for staining histology specimens with the H&E stain and Example II gives an example of a "total exposure" sufficient to accomplish each step. It closely approximates the procedure employed in Example I for performing the pap stain of cytology specimens except that fewer stains are employed.

EXAMPLE II (a) An optional step of prewashing with dehydrating solution for removal of any chemical residues from the preliminary, manual, deparaffinization step;

| (1) | Spray | about 4 seconds |
|---|---|---|
|  | Wait | about 2 seconds |
| (2) | Spray | about 2 seconds |
|  | Wait | about 2 seconds |
| (3) | Spray | about 2 seconds |
|  | Wait | about 2 seconds |
| (2) | Spray | about 2 seconds |
|  | Wait | about 2 seconds |
| (5) | Spray | about 2 seconds |
|  | Wait | about 2 seconds |
| (6) | Spray | about 2 seconds |
|  | Wait | about 2 seconds |
| (7) | Spray | about 2 seconds |
|  | Wait | about 2 seconds; |
| (8) | Spray | about 2 seconds |
|  | Wait | about 2 seconds; |

(b) Washing with bluing-washing solution to remove dehydrating solution and to hydrate the specimen;

| (1) | Spray | about 4 seconds |
|---|---|---|
|  | Wait | about 4 seconds |
| (2) | Spray | about 4 seconds |
|  | Wait | about 4 seconds; |
| (3) | Spray | about 4 seconds |
|  | Wait | about 4 seconds |
| (4) | Spray | about 4 seconds |
|  | Wait | about 4 seconds; |
| (5) | Spray | about 4 seconds |
|  | Wait | about 4 seconds |

(c) Applying Hematoxylin stain;

| (1) | Spray | about 4 seconds |
|---|---|---|
|  | Wait | about 20 seconds |
| (2) | Spray | about 2 seconds |
|  | Wait | about 20 seconds |
| (3) | Spray | about 2 seconds |
|  | Wait | about 12 seconds |
| (4) | Spin | about 1 second at about 1000 RPM to clear excess reagent from slide |
| (5) | Stabilize | about 12 seconds, then reset to about 30 RPM; |

(d) Exposing the specimen to bluing solution to raise the pH to above about 5.0, turn the hematoxylin blue, and wash away excess reagent;

| (1) | Spray | about 6 seconds |
|---|---|---|
|  | Wait | about 10 seconds |
| (2) | Spray | about 4 seconds |
|  | Wait | about 10 seconds |

(e) Staining cytoplasmic elements of the specimen red by exposing the specimen to eosin Y;

| (1) | Spray | about 4 seconds |
|---|---|---|
|  | Wait | about 20 seconds |
| (2) | Spray | about 2 seconds |
|  | Wait | about 20 seconds |

| (3) | Spray | about 2 seconds |
|---|---|---|
|  | Wait | about 18 seconds |
| (4) | Spin | about 1 second at about 1000 RPM to clear excess reagent from slide |
| (5) | Stabilize | about 12 seconds, then reset to about 30 RPM; |

(f) Washing with dehydrating solution to remove excess stain;

| (1) | Spray | about 10 seconds |
|---|---|---|

(g) Performing a drying-clearing step to at least partially dry the slide of dehydrating solution and thereby readying it for the application of a cover-slip mountant and a cover-slip;

| (1) | Spin | about 6 seconds at about 1000 RPM |
|---|---|---|

For the automated spray staining of both cytology and histology specimens, it should be understood that some variation in the centrifuge speed, the spray times and the wait times may be made and that the invention encompasses such variations. Also, while the illustrative embodiments describe a pap spray staining method for cytology specimens and an H&E spray staining method for histology specimens, it is understood that the time-saving and chemical-saving innovations of the invention apply to other cytology and histology staining methods.

Where the claims are directed to a step in the staining process, it is understood that the step may comprise a single step where a combination of reagents are applied or sequential steps where more than one reagent or combination of reagents is applied. Likewise, it is understood that where a step is replaced by an improved step for performing a stain, each occurrence of the step in the staining procedure is replaced. Where the claims are directed to performing a staining method using spray staining equipment, it is understood that any equipment capable of applying reagents by spraying is contemplated whether automated or not. Accordingly, it is understood that claims directed to such spray staining equipment, although they include automated spray staining equipment such as the Aerospray ® stainer, are not limited to such equipment.

Accordingly, whereas this invention is here illustrated and described with reference to embodiments thereof presently contemplated as the best modes of carrying out such invention in actual practice, it is to be understood that various changes may be made in adapting the invention to different embodiments without departing from the broader inventive concepts disclosed herein and comprehended by the claims that follow.

We claim:

1. In a method for carrying out the staining of histology or cytology specimens adhered to a slide free of paraffin mounting, which method includes the following steps:
an optional step of hydrating the specimen adhered to a slide by applying water thereto;
applying excess stain to the specimen;
removing excess stain and/or water by exposing the specimen to a washing-dehydrating reagent;

clearing the specimen of residual washing-dehydrating reagent remaining from a previous washing-dehydrating step and thereby readying the specimen and slide for the application of a cover-slip mountant and a cover-slip;

the improvement comprising:

clearing the specimen by performing a drying-clearing step wherein the specimen is at least partially dried of the washing-dehydrating reagent thereby readying it for the application of a cover-slip mountant and a cover-slip without a chemical-clearing step.

2. A method according to claim 1 wherein the drying-clearing step is accomplished by applying forced air.

3. A method according to claim 1 wherein the drying-clearing step is accomplished by applying mild heat.

4. A method according to claim 1 wherein the drying-clearing step is accomplished by exposing the specimen to ambient evaporator hood or room conditions.

5. A method according to claim 1 wherein the drying-clearing step is performed in staining equipment including means for applying centrifugal force and the drying-clearing step is achieved by centrifugation.

6. A method according to claim 5, the improvement additionally comprising:

exposing a specimen to washing-dehydrating reagent to remove water and/or excess stain after said specimen has had water and/or excess stain applied to it by spraying the slide with an essentially anhydrous solution of washing-dehydrating reagent.

7. In a method according to claim 6, wherein there is additionally included the step of staining the specimen with hematoxylin after a hydration step and prior to any additional staining steps wherein an excess of hematoxylin is provided, the improvements additionally comprising:

removing excess hematoxylin after said hematoxylin has been applied to said specimen by spraying the slide with a combination bluing-washing solution having a concentration of a basic salt solute of about 0.01 molar yielding a solution with above about pH 5.0; and raising the pH of the slide for the application of any subsequent reagent.

8. A method of carrying out a Papanicolaou stain according to claim 7 wherein the spraying is performed by automated spray staining equipment including a centrifuge carousel for holding the slides and rotating them past a spraying apparatus at a selectable rotational speed, said equipment being capable of administering alternating cycles of 1) spraying a reagent on a specimen and 2) waiting for the applied reagent to diffuse through and interact with the specimen, the number of cycles and total length of time of each of said cycles of spraying and waiting comprising a total exposure of a specimen to a reagent, said method comprising the sequential steps of:

(a) exposing the specimen to washing-dehydrating reagent, the total exposure being sufficient to wash from the specimen any unwanted chemical residues that may be present in the specimen;

(b) exposing the specimen to a combination bluing-washing solution, i.e., a hydrating step, the total exposure being sufficient to remove the washing-dehydrating reagent and hydrate the specimen;

(c) staining the specimen with hematoxylin stain by exposing it to an excess of said stain, the total exposure being sufficient to stain susceptible elements of the cells of the specimen with hematoxylin; followed by resetting to a higher rotational speed and spinning for a sufficient period of time to remove excess reagent; followed by waiting for a sufficient length of time to stabilize the carousel so that the rotational speed can be reset to a speed suitable for spray application; followed by exposing the specimen to a combination bluing-washing solution, the total exposure being sufficient to wash off remaining excess hematoxylin and raise the pH of the specimen to above 5.0 thereby turning the hematoxylin blue;

(d) staining the specimen with orange G stain by exposing said specimen to said stain, the total exposure being sufficient to stain keratinized cells of the specimen yellow to orange; followed by resetting to a higher rotational speed and spinning for a sufficient period of time to partially remove excess stain; followed by waiting for a sufficient length of time to stabilize the carousel so that the rotational speed can be reset to a speed suitable for spray application;

(e) exposing the specimen to washing-dehydrating reagent, the total exposure being sufficient to wash away excess orange G stain;

(f) staining the specimen with Papanicolaou EA stain by exposing the specimen to Papanicolaou EA stain, the total exposure being sufficient to stain differing elements of said specimen susceptible to said stain either red or blue; followed by resetting to a higher rotational speed and spinning for a sufficient period of time to partially remove excess stain; followed by waiting for a sufficient length of time to stabilize the carousel so that the rotational speed can be reset to a speed suitable for spray application;

(g) exposing the specimen to washing-dehydrating reagent the total exposure being sufficient to wash away excess EA stain;

(h) performing a drying-clearing step by spinning for a sufficient period of time to clear excess reagent and at least partially dry the specimen of washing-dehydrating reagent thereby readying the slide for the application of a cover-slip mountant and cover-slip.

9. A method for carrying out a hematoxylin and eosin stain according to claim 7 wherein the spraying is performed by automated spray staining equipment including a centrifuge carousel for holding the slides and rotating them past a spraying apparatus at a selectable rotational speed, said equipment being adapted to administer alternating cycles of 1) spraying a reagent on a specimen and 2) waiting for the applied reagent to diffuse through and interact with the specimen, the number of cycles and the total length of time of each of said cycles of spraying and waiting comprising a total exposure of a specimen to a reagent, said method comprising the steps of:

(a) exposing the specimen to washing-dehydrating reagent, the total exposure being sufficient to wash from the specimen any unwanted residues;

(b) exposing the specimen to bluing-washing solution, the total exposure being sufficient to remove the washing-dehydrating reagent and hydrate the specimen;

(c) staining the specimen with hematoxylin by exposing it to said stain, the total exposure being sufficient to stain the susceptible elements of the cells of the specimen with hematoxylin; followed by resetting to a higher rotational speed and spinning for a sufficient period of time to remove excess reagent; followed by waiting for a sufficient length of time to stabilize the carousel so that the rotational speed can be reset to a speed suitable for spray application, followed by exposing the specimen to bluing-washing solution, the total exposure being sufficient to wash off remaining excess hematoxylin and raise the pH of the specimen to above 5.0 And thereby turn the hematoxylin blue;

(d) staining the specimen with eosin Y stain by exposing the specimen to said stain, the total exposure being sufficient to stain the element susceptible to said stain red; followed by resetting to a higher rotational speed and spinning for a sufficient period of time to remove excess reagent; followed by waiting for a sufficient length of time to stabilize the carousel so that the rotational speed can be reset to a speed suitable for spray application;

(e) exposing the specimen to washing-dehydrating reagent, the total exposure being sufficient to wash away excess eosin Y stain;

(f) performing a drying-clearing step by spinning for a sufficient period of time to clear excess reagent and at least partially dry the specimen of the washing-dehydrating reagent thus readying the slide for the application of a cover-slip mountant and cover-slip.

10. In a method for carrying out the staining of histology or cytology specimens whereby the following steps are included:

exposing a slide having a specimen fixed to it to a washing-dehydrating reagent;

removing washing-dehydrating reagent and hydrating the specimen by exposing the slide to an aqueous reagent;

staining susceptible elements of the cells of the specimen with hematoxylin by exposing the specimen to an excess of said stain, removing excess stain by exposing the specimen to an aqueous reagent, exposing the specimen to a bluing solution having a pH above 5.0 to turn the hematoxylin blue and readying the specimen for the application of subsequent reagents;

removing the excess stain and/or water by exposing the specimen to a washing-dehydrating reagent remaining from a previous washing-dehydrating step and thereby readying the specimen and slide for the application of a cover-slip mountant and a cover-slip; and clearing the specimen of residual washing-dehydrating reagent remaining from a previous washing-dehydrating step and thereby readying the slide for the application of a cover-slip mountant and a cover-slip;

the improvement comprising:

exposing the slide to a combination bluing-washing solution having a concentration of a basic salt solute of about 0.01 molar yielding a solution with above about pH 5.0, said exposure raising the pH of the specimen above pH 5.0 thereby turning the hematoxylin blue, washing away excess hematoxylin, and readying the specimen for application of a subsequent reagent.

11. A method according to claim 10 wherein the solute is sodium bicarbonate.

12. A method according to claim 10 wherein the improvement additionally comprises:

clearing residual washing-dehydrating solution remaining from the washing step from the specimen by at least partially drying residual washing-dehydrating from the specimen and thereby readying the slide for the application of a cover-slip mountant and a cover-slip.

13. A method according to claim 10, the improvements additionally comprising:

exposing the slide to washing-dehydrating reagent by spraying said slide with an essentially anhydrous washing-dehydrating reagent solution.

14. In a method for carrying out the staining of a histology or cytology specimen including the step of applying to a slide having a specimen affixed thereto, a reagent, other than a washing-dehydrating reagent, the improvement comprising:

removing said reagent from the specimen by repeatedly spraying the slide with an essentially anhydrous washing-dehydrating reagent.

15. A method according to claim 14, wherein the washing-dehydrating reagent is selected from the group consisting of glycols, ketones, esters and ethers of 2 to 5 carbon atoms, alcohols of 1 to 3 carbon atoms, and mixtures thereof.

16. A method according to claim 14, wherein the washing-dehydrating reagent consists of essentially anhydrous ethanol, other essentially anhydrous alcohols of from 1 to 3 carbon atoms, and mixtures thereof.

17. A method of readying for the application of a cover-slip mountant and a cover-slip a histology or cytology specimen that has been affixed to a slide and to which stain and/or water has been applied and excess stain and/or water removed by application of a washing-dehydrating reagent, comprising the step of at least partially drying the washing-dehydrating reagent applied to the specimen thereby readying the specimen and slide for application of a cover-slip mountant and cover-slip without a chemical clearing step.

18. In a method for carrying out the staining of histology or cytology specimens wherein is included the step of staining the susceptible elements of the specimen with hematoxylin wherein an excess of hematoxylin is provided, the improvements comprising:

removing excess hematoxylin by spraying the slide with a combination bluing-washing solution having a concentration of a basic salt solute of no more than about 0.01 molar yielding a solution with above about pH 5.0 and raising the pH of the slide to above pH 5.0 thereby turning the hematoxylin blue and readying the slide for the application of a subsequent reagent.

19. A method according to claim 18 wherein the basic salt solute is sodium bicarbonate.

* * * * *